United States Patent [19]

Thornfeldt et al.

[11] Patent Number: 4,889,850

[45] Date of Patent: Dec. 26, 1989

[54] TREATMENT OF COLIC AND TEETHING

[76] Inventors: Carl R. Thornfeldt, 1054 NW. 2nd Ave.; Robert E. Thornfeldt, 1021 SW. 5th Ave., both of Ontario, Oreg. 97914

[21] Appl. No.: 291,475

[22] Filed: Dec. 28, 1988

Related U.S. Application Data

[63] Continuation of Ser. No. 48,275, May 11, 1987, abandoned.

[51] Int. Cl.⁴ .................... A61K 31/55; A61K 31/495
[52] U.S. Cl. ..................................... 514/221; 514/255
[58] Field of Search .................. 514/255, 221; 424/49, 424/54

[56] References Cited

U.S. PATENT DOCUMENTS

| | | | |
|---|---|---|---|
| 2,899,436 | 8/1959 | Morren | 260/268 |
| 3,109,843 | 11/1963 | Reeder et al. | 260/239 |
| 3,136,815 | 7/1964 | Reeder et al. | 260/562 |
| 3,371,085 | 2/1968 | Reeder et al. | 260/239.3 |
| 4,734,412 | 3/1988 | Kessler | 514/221 |

OTHER PUBLICATIONS

J. M. Clifford, "Determination of Two Benzodiazepine Anticonvulsants In The Plasma . . .", *Methodol. Dev. Biochem.,* 1976, vol. 5, pp. 203–209.

E. Czarnecka et al., *"Polish Soc. of Electroencephalography and Clinical Neurophysiology",* (Neth.), 1987, vol. 45(3), pp. 7P–8P.

*Primary Examiner*—Stanley J. Friedman
*Assistant Examiner*—Zohreh A. Fay
*Attorney, Agent, or Firm*—Townsend and Townsend

[57] ABSTRACT

Teething and colic are alleviated in infants and toddlers by the administration of a combination of an antihistamine and a benzodiazepine having sedative hypnotic activity. An exemplary antihistamine is hydroxyzine pamoate, and an exemplary benzodiazepine is diazepam.

13 Claims, No Drawings

TREATMENT OF COLIC AND TEETHING

This is a continuation of application Ser. No. 048,275, filed May 11, 1987, now abandoned.

BACKGROUND OF THE INVENTION

This invention relates to the treatment of colic and teething, two conditions that afflict a significant portion of babies and young children.

Colic is a symptom complex characterized by paroxysms of presumably severe abdominal pain and crying with irritability and fussing in an otherwise healthy infant. These episodes usually occur during the first one and one-half to nine months of life and afflict up to 40% of infants. There are a number of known and presumed causes of this condition including milk allergy, under feeding, over feeding, high carbohydrate diet, ineffective burping, excessively large holes in the nipple, excess air sucked in, changes in handling, feeding, and sleeping routines, stimulus overload, anxious parents, and gastrointestinal smooth muscle cramping. To be effective, therapeutic drugs must do more than merely relieve pain, since pain plays a minor role if any in colic.

Teething is another symptom complex occurring in nearly all infants and toddlers to some degree at three to eighteen months of age. Teething is characterized by pain, tenderness, edema, excess salivation, irritability and insomnia. These symptoms result from migration and eventual eruption of deciduous teeth through the oral mucosa.

Current therapies for colic are generally discouraging, especially for severe episodes. On a short-term basis, mechanical maneuvers such as rhythmic motions are often beneficial. Pharmaceutical intervention, however, should be reserved for prolonged episodes, i.e., those exceeding three weeks. Attempts with the latter have included sedation with either antihistamines or phenobarbital, a long-acting barbiturate. Unfortunately, these have met with limited success. Phenobarbital is particularly undesirable since it usually produces excessive irritability when the sedation subsides.

Another seemingly likely candidate would be dicyclomine, a tertiary amine with antimuscarinic activity that has a published efficacy of 63%. Unfortunately, dicyclomine is limited by a narrow margin of safety due to its known induction of apnea, seizures, and coma. As a result, it is absolutely contraindicated in babies less than six months of age.

In the case of teething, known therapies include providing firm, blunt or cool objects for the baby to bite on, and very short-acting topical anesthetics. There are no other treatment regimens except sedation.

Two combinations of an antihistamine with a barbiturate have been used in the treatment of teething and colic and have demonstrated efficacy for both conditions.

The first is the combination of diphenhydramine (2-diphenylmethoxy-N,N-dimethylethanamine hydrochloride; available from Parke Davis & Co., Morris Plains, N.J., as Benadryl Elixir) and butabarbital sodium (5-ethyl-5-(1-methylpropyl)-2,4,6(1H,3H,5H)-pyrimidinetrione sodium salt; available from Wallace Laboratories, Cranbury, N.J., in both powder form and as Butisol Elixir). The combination has been formulated by mixing 650 mg butabarbital sodium powder in enough water to form a paste, then combining the paste with 120 mL of Benadryl Elixir which contains 12.5 mg diphenhydramine per 5 mL including 14% ethanol, and finally adding 3 drops of hydrochloric acid to clear the solution. The dosage is ½–1 teaspoonful diluted in ½-ounce milk or juice administered orally at the onset of symptoms and repeated every 4–8 hours as needed.

The second combination is that of promethazine hydrochloride (N,N,α-trimethyl-10H-phenothiazine-10-ethanamine; available from Wyeth Laboratories, Philadelphia, Pa., as Phenergan syrup) and butabarbital sodium. This combination has been formulated by mixing equal parts of Butisol Elixir (which contains 30. mg butabarbital sodium per 5 mL including 7% ethanol) and Phenergan syrup (which contains 6.25 mg promethazine hydrochloride per 5 mL including 7% ethanol). The dosage is 1–2 teaspoonsful administered orally at the onset of symptoms and repeated every 4–8 hours as needed.

These two combinations have been administered by the inventors herein as therapy to patients in a pediatrician's office in Ontario, Oreg., as part of their practice in pediatrics over a period of fifteen years prior to the filing date of the present application.

SUMMARY OF THE INVENTION

It has now been discovered that the combination of an antihistamine and a benzodiazepine having sedative hypnotic activity is effective as a therapeutic composition for teething, colic or both.

DETAILED DESCRIPTION OF THE INVENTION

In specific terms, the antihistamines contemplated within the present invention are histamine 1 receptor antagonists. Those of greatest interest in the present invention are the class known as ataractics, i.e., species displaying activity against ataraxia. Preferred among this class are cyclizine derivatives, notably those having the formula

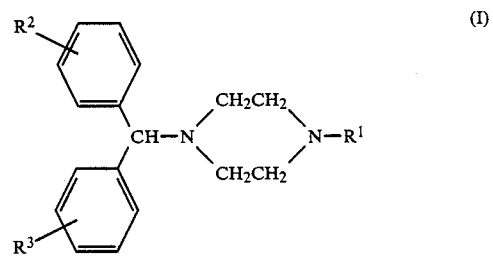

in which:

$R^1$ is $C_1$–$C_6$ alkyl, hydroxy-($C_1$–$C_6$ alkyl), hydroxy-($C_1$–$C_6$ alkoxy)-($C_1$–$C_6$ alkyl), phenyl-($C_1$–$C_6$ alkyl), or ($C_1$–$C_6$ alkyl)- phenyl-($C_1$–$C_6$ alkyl); and $R^2$ and $R^3$, which may be the same or different, are a hydrogen atom, a halogen atom, or $C_1$–$C_6$ alkyl; and acid salts thereof.

Within the scope of formula I, certain species are preferred. These are the species in which $R^1$ is $C_1$–$C_3$ alkyl, hydroxy-($C_1$–$C_3$ alkyl), hydroxy-($C_1$–$C_3$ alkoxy)-($C_1C_3$ alkyl), phenyl-($C_1$–$C_3$ alkyl) or (C–$C_4$ alkyl)-phenyl-($C_1$–$C_3$ alkyl); and $R^2$ and $R^3$ are a hydrogen atom, a chlorine atom, a bromine atom or $C_1$–$C_3$ alkyl.

Further preferred are those in which $R^1$ is methyl, hydroxyethoxyethyl or ($C_1$–$C_4$ alkyl)-phenylmethyl; $R^2$ is a hydrogen atom, a chlorine atom or a bromine atom; and $R^3$ is a hydrogen atom.

In this disclosure, the term "alkyl" is intended to encompass both straight-chain and branched-chain groups. The term "halogen" is intended to include fluorine, chlorine, bromine and iodine atoms only. Term "acid salts" is intended to encompass both mineral acids and organic acids. Preferred acid salts are hydrochlorides, lactates and pamoates.

Examples of cyclizine derivatives within the scope of formula I and useful in the present invention are as follows (generic name followed by Chemical Abstracts name and substituents for formula I):

buclizine dihydrochloride; 1-[(4-chlorophenyl)phenyl-methyl]-4-[[4-(1,1-dimethylethyl)phenyl)methyl]-piperazine dihydrochloride;

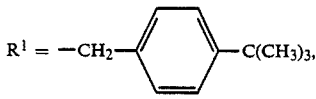

$R^2$=4—Cl, $R^3$=H chlorcyclizine hydrochloride; 1-[(4-chlorophenyl)-phenylmethyl]-4-methylpiperazine hydrochloride; $R^1$=$CH_3$, $R^2$=4—Cl, $R^3$=H cyclizine hydrochloride; 1-diphenylmethyl-4-methyl-piperazine hydrochloride; $R^1$=$CH_3$, $R^2$=H, $R^3$=H cyclizine lactate; 1-diphenylmethyl-4-methylpiperazine lactate; $R^1$=$CH_3$, $R^2$=H, $R^3$=H hydroxyzine hudrochloride; 2-[2-[4-[(4-chlorophenyl)phenylmethyl]-1-piperazinyl]ethoxy]ethanol hydrochloride; $R^1$=—$CH_2CH_2OCH_2CH_2OH$, $R^2$=4—Cl, $R^3$=H hydroxyzine pamoate; 2-[2-[4-[(4-chlorophenyl)-phenylmethyl]-1-piperazinyl]ethoxy]ethanol pamoate; $R^1$=—$CH_2CH_2OCH_2CH_2OH$, $R^2$=4—Cl, $R^3$=H meclizine hydrochloride; 1-[(4-chlorophenyl) phenylmethyl]-4-[(3-methylphenyl)methyl]piperazine hydrochloride;

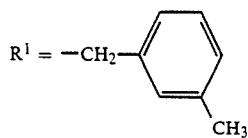

$R^2$=4—Cl, $R^3$=H Each of the examples in the list is a known, commercially available material.

Preferred among the benzodiazepines of the combination of the present invention are those having the formula

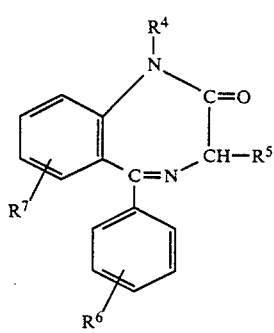

(II)

in which $R^4$ is a hydrogen atom, $C_1$-$C_6$ alkyl, $C_3$-$C_6$ cycloalkyl, $C_1$-$C_6$ haloalkyl, amino-($C_1$-$C_6$ alkyl), ($C_1$-$C_3$ alkylamino)-($C_1$-$C_6$ alkyl), or di($C_1$-$C_3$ alkylamino)-($C_1$-$C_6$ alkyl);

$R^5$ is a hydrogen atom, hydroxy or carboxy;

$R^6$ is a hydrogen atom, a halogen atom or $C_1$-$C_6$ alkyl; and $R^7$ is a hydrogen atom, a halogen atom or $C_1$-$C_6$ alkyl; and salts thereof.

Preferred species within the scope of formula II are those in which $R^4$ is hydrogen, $C_1$-$C_3$ alkyl, cyclopropyl-($C_1$-$C_3$ alkyl), $C_1$-$C_3$ alkyl substituted by 1 to 3 halogen atoms, and di-($C_1$-$C_3$ alkyl)-amino-($C_1$-$C_3$ alkyl); $R^5$ is hydrogen, hydroxy or carboxy; $R^6$ is a hydrogen or halogen atom; and $R^7$ is a hydrogen or halogen atom.

Further preferred are those in which $R^4$ is hydrogen, methyl, cyclopropylmethyl, 2,2,2-trifluoroethyl, and diethylaminoethyl; $R^5$ is hydrogen, hydroxy or carboxy; $R^6$ is a hydrogen or chlorine atom; and $R^7$ is a chlorine atom.

The explanations given above for "alkyl" and "halogen" apply here as well. In addition, the term "haloalkyl" is intended to include alkyl groups with multiple halogen substitutions as well as single substitutions, the multiple halogens being the same or different and preferably up to three per alkyl group. The term "carboxy" refers to the —COOH group. The term "salt" is intended to encompass both acid and alkali salts, examples of the latter being alkali metal salts, with sodium and potassium preferred.

Examples of benzodiazepines within the scope of formula II and useful in the present invention are as follows (generic name followed by Chemical Abstracts name and substituents for formula II):

diazepam; 7-chloro-1,3-dihydro-1-methyl-5-phenyl-2H-1,4-benzodiazepin-2-one; $R^4$=$CH_3$, $R^5$=H, $R^6$=H, $R^7$=7—Cl (the 7-position being defined as the position meta with respect to the carbon to which the —C=N— group is attached)

oxazepam; 7-chloro-1,3-dihydro-3-hydroxy-5-phenyl-2H-1,4-benzodiazepin-2-one; $R^4$=H, $R^5$=OH, $R^6$=H, $R^7$=7—Cl clorazepate dipotassium; 7-chloro-2,3-dihydro-2,2-dihydroxy-5-phenyl-1H-1,4-benzodiazepine-3-carboxylic acid, dipotassium salt; $R^4$=H, $R^5$=COOH, $R^6$=2'—Cl (the 2'-position being defined as the ortho position on the lower phenyl ring), $R^7$=7—Cl prazepam; 7-chloro-1-(cyclopropylmethyl)-1,3-dihydro-5-phenyl-2H-1,4-benzodiazepin-2-one;

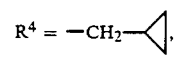

$R^5$=H, $R^6$=H, $R^7$=7—Cl lorazepam; 7-chloro-5-(o-chlorophenyl)-1,3-dihydro-3-hydroxy-2H-1,4-benzodiazepin-2-one; $R^4$=H, $R^5$=OH, $R^6$=2'—Cl, $R^7$=7—Cl halazepam; 7-chloro-1-(2,2,2-trifluoroethyl)-1,3-dihydro-5-phenyl-2H-1,4-benzodiazepin-2-one; $R^4$=—$CH_2CF_3$, $R^5$=H, $R^6$=H, $R^7$=7—Cl flurazepam hydrochloride; 7-chloro-1-[2-(diethylamino)ethyl]-5-(o-fluorophenyl)-1,3-dihydro-2H-1,4-benzodiazepin-2-one hydrochloride; $R^4$=—$CH_2CH_2N(C_2H_5)_2$, $R^5$=H, $R^6$=2'—F, $R^7$=7—Cl Each of the examples in this list is a known, commercially available material.

The term "therapeutically effective amount" is used herein to denote any amount which will cause a substantial improvement in the condition for which the subject is being treated when administered to the subject either in a single dose or repeated doses over a period of time. The amount will vary with whether colic, teething or both are being treated, the degree of severity of the condition, the age and size of the subject, and the type and concentration of formulation applied. Appropriate amounts in any given instance will be readily apparent to those skilled in the art or capable of determination by routine experimentation.

The ratios of the two components of the present invention are not critical and may be varied over a wide range. Best results will generally be achieved when the mole ratio of antihistamine to benzodiazepine is about 0.05 to about 2.0, preferably about 0.1 to about 1.0, most preferably about 0.1 to about 0.5.

Oral administration is preferred. A unit dose constituting a therapeutically effective amount for oral administration will generally fall within about 0.1 mg to about 20 mg of the combination. Formulations known to those skilled in the art for oral administration may be used. Exemplary formulations are solutions, suspensions and emulsions involving palatable liquids bearing a concentration whereby the unit dose amounts to approximately 0.1 to 10 milliliters.

As an optional variation, ethanol may be included in the formulation for enhanced activity.

The following example is offered for illustrative purposes, and is intended neither to limit nor define the invention in any manner.

EXAMPLE

Two groups of patients, each group consisting of four infants or toddlers, each suffering from colic, teething or both, were treated as follows.

A formulation was prepared by grinding one 20 mg tablet of diazepam (Roche Laboratories, Nutley, N.J.) into a fine powder, and suspending the powder in 50 mL of hydroxyzine oral suspension (Pfizer Laboratories, New York, N.Y.). Each 0.5 mL dose thus consisted of 0.2 mg of diazepam and 2.5 mg of hydroxyzine.

A 0.5 mL dose of the formulation was administered to each patient at the onset of symptoms of colic or teething and repeated every 3 to 4 hours if the symptoms recurred. In all patients significant or complete relief of symptoms occurred within fifteen to thirty minutes.

The foregoing description is offered primarily for purposes of illustration. It will be readily apparent to those skilled in the art that numerous variations in both the formulations and their method of use beyond those described above may be made without departing from the spirit and scope of the invention.

What is claimed is:

1. A method for the treatment of a subject suffering from a condition selected from the group consisting of teething and colic, said method comprising administering to said subject a therapeutically effective amount of a composition comprising an ataractic and a benzodiazepine having sedative hypnotic activity; said ataractic having the formula

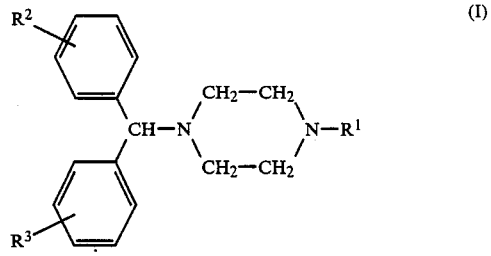

wherein $R^1$ is a member selected from the group consisting of $C_1$–$C_6$ alkyl, hydroxy-($C_1$–$C_6$ alkyl), hydroxy-($C_1$–$C_6$ alkoxy)-($C_1$–$C_6$ alkyl), phenyl-($C_1$–$C_6$ alkyl), and ($C_1$–$C_6$ alkyl)-phenyl-($C_1$–$C_6$ alkyl); and $R^2$ and $R^3$ are members independently selected from the group consisting of a hydrogen atom, a halogen atom, and $C_1$–$C_6$ alkyl; or an acid salt thereof; and said benzodiazepine having the formula

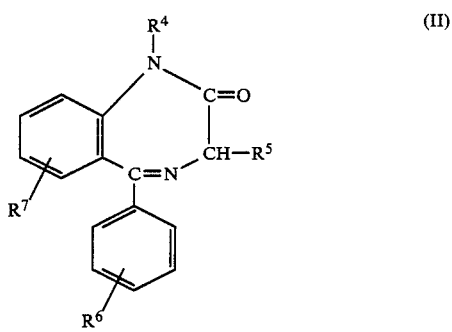

wherein $R^4$ is a member selected from the group consisting of hydrogen, $C_1$–$C_6$ alkyl, $C_3$–$C_6$ cycloalkyl, $C_1$–$C_6$ haloalkyl, amino-($C_1$–$C_6$ alkyl), ($C_1$–$C_3$ alkylamino)-($C_1$–$C_3$ alkyl), and di-($C_1$–$C_3$ alkyl)-amino-($C_1$–$C_6$ alkyl); $R^5$ is a member selected from the group consisting of a hydrogen atom, hydroxy, and carboxy; $R^6$ is a member selected from the group consisting of a hydrogen atom, a halogen atom, and $C_1$–$C_6$ alkyl; and $R^7$ is a member selected from the group consisting of a hydrogen atom, a halogen atom, and $C_1$–$C_6$ alkyl; or a salt thereof; and the mole ratio of said ataractic to said benzodiazepine being from about 0.05 to about 2.0.

2. A method in accordance with claim 1 in which $R^1$ is a member selected from the group consisting of $C_1$–$C_3$ alkyl, hydroxy-($C_1$–$C_3$ alkyl), hydroxy-($C_1$–$C_3$ alkoxy)-($C_1$–$C_3$ alkyl), phenyl-($C_1$–$C_3$ alkyl), and ($C_1$–$C_4$ alkyl)-phenyl-($C_1$–$C_3$ alkyl); and $R^2$ and $R^3$ are members independently selected from the group consisting of a hydrogen atom, a chlorine atom, a bromine atom, and $C_1$–$C_3$ alkyl.

3. A method in accordance with claim 1 in which $R^1$ is a member selected from the group consisting of methyl, hydroxyethoxyethyl, and ($C_1$–$C_4$ alkyl)-phenylmethyl; $R^2$ is a member selected from the group consisting of a hydrogen atom, a chlorine atom and a bromine atom; $R^3$ is a hydrogen atom; and said acid salt is a member selected from the group consisting of a hydrochloride salt, a lactate salt and a pamoate salt.

4. A method in accordance with claim 1 in which $R^1$ is hydroxyethoxyethyl, $R^2$ is 4-chloro, $R^3$ is a hydrogen atom, and said compound is the pamoate salt thereof.

5. A method in accordance with claim 1 in which $R^4$ is a member selected from the group consisting of a hydrogen atom, $C_1$–$C_3$ alkyl, cyclopropyl-($C_1$–$C_3$ alkyl), $C_1$–$C_3$ alkyl substituted by 1 to 3 halogen atoms, and di-($C_1$–$C_3$ alkyl)-amino-($C_1$–$C_3$ alkyl); $R^5$ is a member selected from the group consisting of a hydrogen atom, hydroxy, and carboxy; $R^6$ is a member selected from the group consisting of a hydrogen atom and a halogen atom; and $R^7$ is a member selected from the group consisting of a hydrogen atom and a halogen atom.

6. A method in accordance with claim 1 in which $R^4$ is a member selected from the group consisting of a hydrogen atom, methyl, cyclopropylmethyl, 2,2,2-trifluoroethyl, and diethylaminoethyl; $R^5$ is a member selected from the group consisting of a hydrogen atom, hydroxy, and carboxy; $R^6$ is a member selected from the group consisting of a hydrogen atom and a chlorine atom; and $R^7$ is a chlorine atom.

7. A method in accordance with claim 1 in which $R^4$ is methyl, $R^5$ is a hydrogen atom, $R^6$ is a hydrogen atom, and $R^7$ is a chlorine atom.

8. A method in accordance with claim 1 in which said ataractic is a member selected from the group consisting of hydroxyzine hydrochloride and hydroxyzine pamoate, and said benzodiazepine is a member selected from the group consisting of diazepam and lorazepam.

9. A method in accordance with claim 1 in which said mole ratio is about 0.1 to about 1.0.

10. A method in accordance with claim 1 in which said ataractic is hydroxyzine pamoate and said benzodiazepine is diazepam, and said mole ratio is about 0.1 to about 1.0.

11. A method in accordance with claim 1 in which said ataractic is hydroxyzine pamoate and said benzodiazepine is diazepam and said mole ratio is about 0.1 to about 0.5.

12. A method in accordance with claim 1 in which said ataractic is hydroxyzine pamoate and said benzodiazepine is lorazepam, and said mole ratios is about 0.1 to about 1.0.

13. A method in accordance with claim 1 in which said ataractic is hydroxyzine pamoate and said benzodiazepine is lorazepam, and said mole ratio is about 0.1 to about 0.5.

* * * * *